(12) United States Patent
Kwon et al.

(10) Patent No.: US 9,242,024 B2
(45) Date of Patent: Jan. 26, 2016

(54) THREE-DIMENSIONAL NANOFIBER SCAFFOLD FOR TISSUE REPAIR AND PREPARATION METHOD THEREOF

(75) Inventors: Il Keun Kwon, Seoul (KR); Chun Ho Kim, Seoul (KR); Dae Hyeok Yang, Seoul (KR); Jung Bok Lee, Busan (KR); Ha Na Park, Pohang-si (KR); Sung In Jeong, Chungju-si (KR)

(73) Assignee: UNIVERSITY-INDUSTRY COOPERATION GROUP OF KYUNG-HEE UNIVERSITY ET AL, Yongin-Si, Gyeonggi-Do (KR)

( * ) Notice: Subject to any disclaimer, the term of this patent is extended or adjusted under 35 U.S.C. 154(b) by 146 days.

(21) Appl. No.: 14/008,408

(22) PCT Filed: Mar. 16, 2012

(86) PCT No.: PCT/KR2012/001925
§ 371 (c)(1),
(2), (4) Date: Sep. 27, 2013

(87) PCT Pub. No.: WO2012/134086
PCT Pub. Date: Oct. 4, 2012

(65) Prior Publication Data
US 2014/0024760 A1    Jan. 23, 2014

(30) Foreign Application Priority Data
Mar. 29, 2011    (KR) .................. 10-2011-0028363

(51) Int. Cl.
| | |
|---|---|
| *A61L 27/14* | (2006.01) |
| *C08K 5/05* | (2006.01) |
| *A61L 27/48* | (2006.01) |
| *A61L 27/56* | (2006.01) |
| *C12N 5/00* | (2006.01) |
| *C08L 5/08* | (2006.01) |
| *C08L 89/06* | (2006.01) |

(52) U.S. Cl.
CPC .................. *A61L 27/14* (2013.01); *A61L 27/48* (2013.01); *A61L 27/56* (2013.01); *C08K 5/05* (2013.01); *C08L 5/08* (2013.01); *C08L 89/06* (2013.01); *C12N 5/0068* (2013.01); *A61L 2400/12* (2013.01); *C08L 2205/16* (2013.01); *C12N 2533/40* (2013.01)

(58) Field of Classification Search
CPC ......... A61L 27/14; A61L 27/48; A61L 27/56; A61L 2400/12; C08K 5/05; C12N 5/0068; C12N 2533/40; C08L 5/08; C08L 89/06
See application file for complete search history.

(56) References Cited

U.S. PATENT DOCUMENTS

2013/0197122 A1* 8/2013 Gauchet et al. ............... 522/157

FOREIGN PATENT DOCUMENTS

| KR | 1020090034202 A | 4/2009 |
|---|---|---|
| KR | 1020090041271 A | 4/2009 |
| KR | 1020090127371 A | 12/2009 |
| KR | 1020110009702 A | 1/2011 |
| WO | 2008121338 A2 | 10/2008 |
| WO | 2009045042 A1 | 4/2009 |
| WO | 2009140381 A1 | 11/2009 |

OTHER PUBLICATIONS

International Search Report mailed Oct. 29, 2012, 2012 for PCT/KR2012/001925.

* cited by examiner

*Primary Examiner* — Kriellion Sanders
(74) *Attorney, Agent, or Firm* — Hauptman Ham, LLP

(57) ABSTRACT

The present invention provides a three-dimensional nanofibrous scaffold for tissue regeneration, which is increased in porosity and thickness to enlarge the surface area thereof, thereby enabling cell adhesion at a high density, and a method for fabricating the same. The method for fabricating a three-dimensional nanofibrous scaffold for tissue regeneration includes the steps of: (a) preparing a polymer solution; (b) preparing a nanofiber matrix, in which a plurality of nanofibers is entangled with each other, from the polymer solution prepared in step (a) using electrospinning; and (c) immersing the prepared nanofiber matrix in a solution and subjecting the solution to ultrasonication, thereby increasing the thickness and porosity of the nanofiber matrix. According to the inventive scaffold fabricating method, the nanofiber matrix prepared by using electrospinning is ultrasonicated in a solution, so that a three-dimensional nanofibrous scaffold with improved thickness and porosity can be provided in a simple and low-cost manner.

8 Claims, 8 Drawing Sheets

THREE-DIMENSIONAL NANOFIBER SCAFFOLD FOR TISSUE REPAIR AND PREPARATION METHOD THEREOF

CROSS-REFERENCE TO RELATED APPLICATIONS

This application claims the benefit of Korean Patent Application No. 10-2011-0028363, filed on Mar. 29, 2011 in the Korean Intellectual Property Office, which is incorporated herein by reference in its entirety.

BACKGROUND OF THE INVENTION

1. Field of the Invention

Exemplary embodiments of the present invention relate to a scaffold for tissue regeneration, and more particularly to a three-dimensional nanofibrous scaffold for tissue regeneration, in which can be increased in thickness and porosity in a simple manner by ultrasonication, and a method for fabricating the same.

2. Background of the Related Art

The human body is very limited in tissue's ability to self-regenerate because the tissue has a significantly complex and delicate structure. The human body possesses a possibility of tissues being regenerated when tissues are damaged owing to stem cells, but there may occur the case that goes beyond a limitation of a tissue regeneration function due to the reason of incident, illness, aging, or the like. Recently, the need for regeneration of organs or tissues of the body is sharply increasing since they encounter a limitation of the ability to regenerate due to an increase in a variety of diseases and incidents along with the rapid entry into an aging society.

In addition, the demand for development of a technology capable of effectively replacing or implanting biological tissues is increasing gradually, and an effort to restore organs and tissues of the human body has been greatly spotlighted for a long time. Initially, an effort were attempted for the development of biocompatible materials for an artificial substitute, organ transplantation, and the like, but such a technology is recently advanced to the tissue engineering that incorporates and applies biological science, engineering, and medical science.

The tissue engineering is a field of regenerative medicine which deals with regeneration of body tissues from cells to artificial organs, and is recognized as one of important technologies of a biological science and a medical field in future based on the science that deals with biological and engineering technologies involving biomaterials that can help to restore tissues or organs. A research is in progress on various methods for achieving a goal to restore, maintain, and improve the function of the human body by understanding the correlation between the structure and function of biological tissues, and furthermore fabricating and implanting biological substitutes.

In the tissue engineering, to produce a scaffold that functions as a support to allow cells to adhere and grow is one of core technologies. Unlike a two-dimensional membrane or capsule, the scaffold is formed in a three-dimensional shape and refers to a space where all the cells having a three-dimensional structure in vivo can adhere, proliferate, and differentiate.

The scaffold plays a very important role in the tissue engineering. In addition, the scaffold plays a significant role in growth of cells disseminated in a porous structure and cells migrated from tissue surroundings. Almost all the cells in vivo are adherent cells that adhere and grow. If there is no a place for the cells to adhere, they do not grow but perish. Thus, it is required that the scaffold should provide an environment suitable for adhesion, growth, and differentiation of cells as well as cell migration. The scaffold can be prepared of various materials, and a research is actively being conducted to develop a scaffold for tissue regeneration using a natural material, a synthetic polymer, a biological ceramics, and a polymer-ceramic composite material.

The scaffold has a structure that needs a high porosity to secure a large surface area enabling cell adhesion at a high density, and requires an open cellular structure in which large pores enabling formation of a blood vessel, and delivery of a substance such as nutrient, growth factor, hormone, or the like, after implantation in vivo are connected to each other. In addition, it is required that porosity and the shape of pores of the scaffold should be controlled depending on the properties of tissues cultured.

As examples of a technique for preparing a sponge type porous scaffold, particulate leaching, emulsion freeze-drying, high-pressure gas expansion, phase separation, and the like have been generally accepted. However, such a conventional scaffold preparation method has a limitation in the production of pores having an open cellular structure, and entails a problem in that the pore size is too small to culture cells three-dimensionally.

SUMMARY OF THE INVENTION

Accordingly, the present invention has been made to solve the above-mentioned problems involved in the conventional prior art, and it is an object of the present invention to provide a three-dimensional nanofibrous scaffold for tissue regeneration, which is increased in porosity and thickness to enlarge the surface area thereof, thereby enabling cell adhesion at a high density, and a method for fabricating the same.

To achieve the above object, in one aspect, the present invention provides a method for fabricating a three-dimensional nanofibrous scaffold for tissue regeneration, the method including the steps of:

(a) preparing a polymer solution;

(b) preparing a nanofiber matrix, in which a plurality of nanofibers is entangled with each other, from the polymer solution prepared in step (a) using electrospinning; and (c) immersing the prepared nanofiber matrix in a solution and subjecting the solution to ultrasonication, thereby increasing the thickness and porosity of the nanofiber matrix.

The method for fabricating a three-dimensional nanofibrous scaffold for tissue regeneration according to the present invention may further include adding a natural polymer to the nanofiber matrix by applying a natural polymer solution on the nanofiber matrix and freeze-drying the polymer solution-coated nanofiber matrix after step (c).

The natural polymer may be selected from gelatin and chitosan.

Preferably, in step (c), sonic waves may be applied to the solution in which the nanofiber matrix is immersed in a state in which the solution is cooled.

In step (c), the solution in which the nanofiber matrix is immersed may be cooled with ice.

In step (c), sonic waves may be applied to the solution in which the nanofiber matrix is immersed in a state in which the temperature of the solution is set to 0° C. to 4° C.

The solution used in step (c) may be a natural polymer solution in which a natural polymer is dissolved.

The natural polymer solution may be selected from an aqueous gelatin solution and an aqueous chitosan solution.

In step (a), the polymer solution may be prepared by dissolving a synthetic polymer and a natural polymer in an organic solvent.

To achieve the above object, in another aspect, the present invention provides a three-dimensional nanofibrous scaffold for tissue regeneration fabricated by the above-mentioned method.

According to the method for fabricating a three-dimensional nanofibrous scaffold for tissue regeneration according to the present invention, the nanofiber matrix is prepared through electrospinning, and ultrasonication is performed on the solution in which the prepared nanofiber matrix is immersed, so that a three-dimensional nanofibrous scaffold for tissue regeneration having increased thickness and porosity can be provided in a relatively simple and expensive manner as compared to the conventional prior art.

In addition, the three-dimensional nanofibrous scaffold for tissue regeneration according to the present invention is advantageous in cell culture in that its pore size is large, its porosity is high, and thus its cellular infiltration is excellent.

Moreover, the three-dimensional nanofibrous scaffold for tissue regeneration according to the present invention exhibits excellent biocompatibility and antimicrobial activity of the natural polymer along with excellent mechanical properties and flexibility of the synthetic polymer.

BRIEF DESCRIPTION OF THE DRAWINGS

The above and other objects, features and advantages of the present invention will be apparent from the following detailed description of the preferred embodiments of the invention in conjunction with the accompanying drawings, in which.

Figure 1:
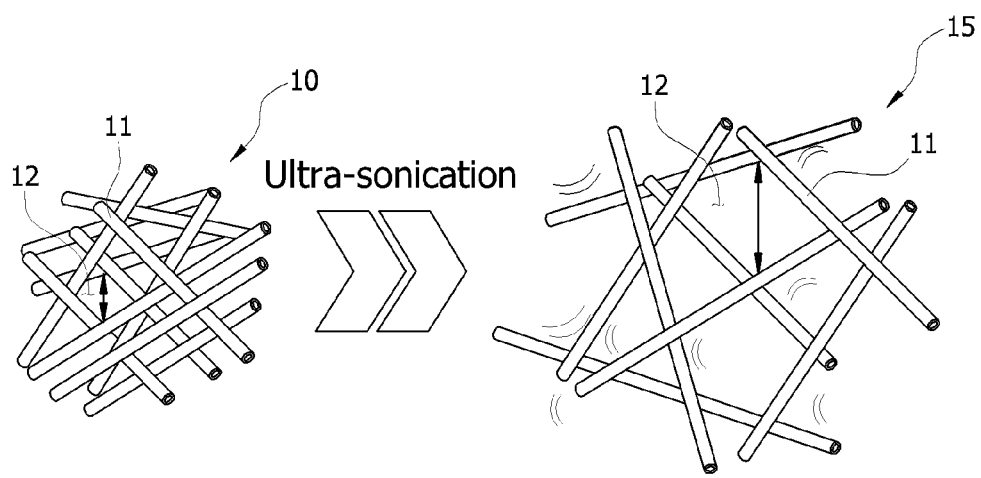
FIG. 1 is a schematic diagram illustrating a process in which a three-dimensional nanofibrous scaffold for tissue regeneration according to the present invention is fabricated by subjecting, a nanofiber matrix prepared by electrospinning, to ultrasonication.

| [Explanation on symbols] | |
|---|---|
| 10: nanofiber matrix | 11: nanofiber |
| 12: pore | 15: three-dimensional nanofibrous scaffold |
| 20: electrospinning device | 21: syringe pump |
| 22: high-voltage DC power supply | 23: needle |
| 24: collector | 30: solution |
| 32: ultrasonic transducer | 34: water tank |
| 36: ice | 38: cooling container |

DETAILED DESCRIPTION OF THE PREFERRED EMBODIMENTS

Now, a three-dimensional nanofibrous scaffold for tissue regeneration and a method for fabricating the same according to the preferred embodiment of the present invention will be described hereinafter in more detail with reference to the accompanying drawings.

In the detailed description of the preferred embodiments of the present invention, the size, the shape, or the like of constituent elements may be exaggeratedly or simplifiedly shown in the drawings for the sake of clarity and convenience of explanation. Also, the following terms are specifically defined in consideration of the constitution and function of the present invention, which may vary according to an intention of a user or an operator or according to custom. Therefore, such terms should be interpreted as the meaning and concept conforming to the technical idea of the present invention based on overall contents of the specification.

FIG. 1 is a schematic diagram illustrating a process in which a three-dimensional nanofibrous scaffold for tissue regeneration according to the present invention is fabricated by subjecting, a nanofiber matrix prepared by electrospinning, to ultrasonication.

Referring to FIG. 1, a three-dimensional nanofibrous scaffold 15 for tissue regeneration according to the present invention has a three-dimensional structure with a thickness, in which a plurality of nanofibers 11 is randomly entangled with each other. Such a three-dimensional nanofibrous scaffold 15 for tissue regeneration can be fabricated by preparing a nanofiber matrix 10 using electrospinning and subjecting the nanofiber matrix 10 to ultrasonication to expand pores 12 and increase the porosity and thickness of the nanofiber matrix 10. The nanofibers 11 constituting the three-dimensional nanofibrous scaffold 15 may be composed of a synthetic polymer or a mixed polymer in which a natural polymer is mixed with the synthetic polymer.

The natural polymer is good in biocompatibility and biological activity, but is limited in use in that it has a difficulty in controlling mechanical strength and degradation speed and has a possibility of being contaminated with viruses or the like as being isolated from the tissues of plants, animals, and the human. On the other hand, the synthetic polymer is easy in imparting the characteristics conforming to the use purpose since the physical and chemical properties of a monomer can be controlled in a synthesis process. In addition, the synthetic polymer can control the physical and mechanical properties of a scaffold for the tissue engineering according to the use through the adjustment of the molecular structure and molecular weight thereof.

The synthetic polymer is roughly classified into biodegradable and non-biodegradable. Examples of the biodegradable synthetic poymer include polyvinyl alcohol (PVA), polyhydroxyethyl methacrylate (PHEMA), poly (N-isopropyl acrylamide (PNIPAAm), etc. Examples of the biodegradable synthetic polymer include polyglycolic acid (PGA), polylactic acid (PLA), polypropylene fumarate, poly-ϵ-caprolactone (PCL), polycyanoacrylate, polydioxanone, polyurethane, etc. The biodegradable synthetic polymer has an advantage in that since it degrades to a biological metabolic substance, which is in turn excreted in vitro after inducing the regeneration of a desired tissue, serious toxicity is not produced and foreign substances except the tissue remain no longer at a tissue regeneration site, Particularly, PGA and PLA, and PLGA as a copolymer of the two polymers are non-toxic polymers, which degrade to glycolic acid, lactic acid and are removed in vivo, and thus are widely used as materials for a scaffold for tissue regeneration.

A process for preparing a nanostructure according to the present invention will be now described hereinafter with reference to FIGS. 2 and 3.

Figure 2:
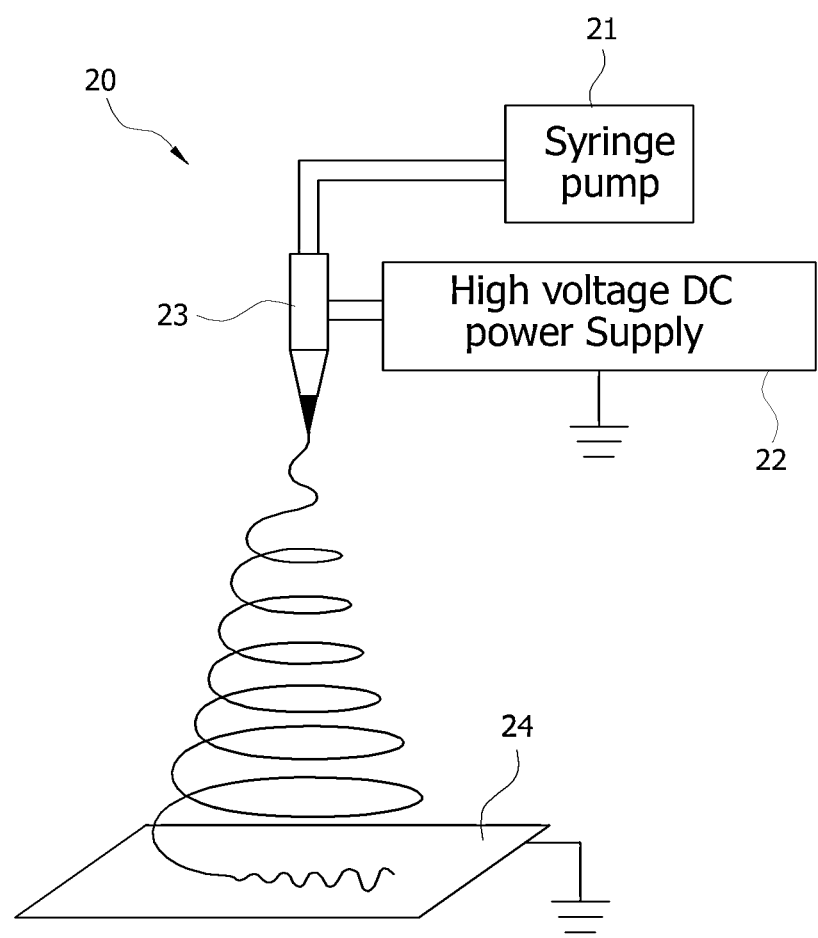
FIG. 2 is a schematic diagram illustrating a process of preparing a nanofiber matrix using an electrospinning device in a method of fabricating a three-dimensional nanofibrous scaffold for tissue regeneration according to the present invention.
Figure 3:
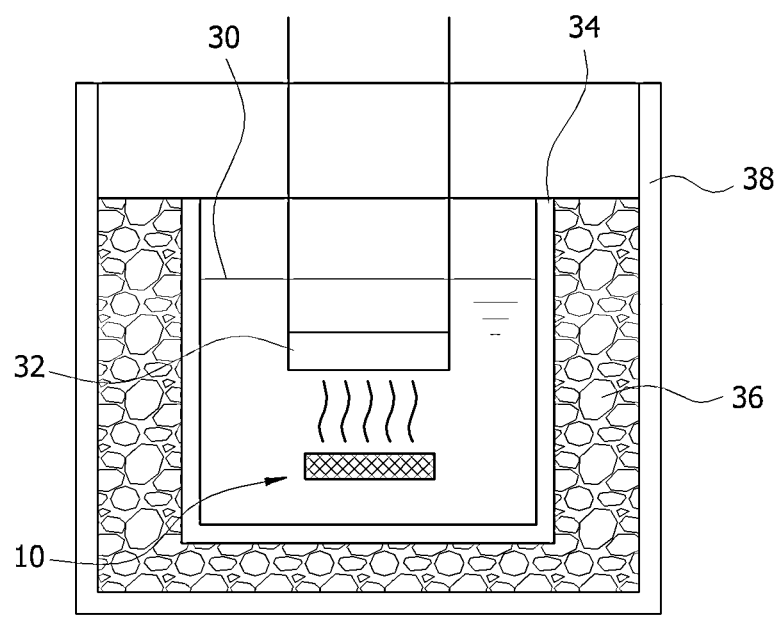
FIG. 3 is a schematic diagram illustrating ultrasonication of a nanofiber matrix in a method of fabricating a three-dimensional nanofibrous scaffold for tissue regeneration according to the present invention.

FIG. 2 is a schematic diagram illustrating a process of preparing a nanofiber matrix using an electrospinning device in a method of fabricating a three-dimensional nanofibrous scaffold for tissue regeneration according to the present invention, and FIG. 3 is a schematic diagram illustrating ultrasonication of a nanofiber matrix in a method of fabricating a three-dimensional nanofibrous scaffold for tissue regeneration according to the present invention.

First, a nanofiber matrix 10 is prepared by dissolving a synthetic polymer, or a synthetic polymer and a natural polymer in an organic solvent to prepare a polymer solution, and spinning the prepared polymer solution by using an electrospinning device. The electrospinning technique is one in which a one-dimensional nano structure material can be implemented in an efficient and low-cost manner. A nanofiber-, nanorod-, or nanotube-shaped material can be fabricated in an easy and low-cost manner by using the electrospinning technique. This electrospinning technique has a basic principle that continuous organic/inorganic nanofibers are formed on a grounded collector while being drawn under a high electric field created on the surface of the polymer solution.

Referring to FIG. 2, an electrospinning device 20 includes a syringe pump 21 that allows a liquid precursor having viscosity to be forcibly pushed, a high-voltage DC power supply 22, a needle 23 for drawing nanofibers, and a grounded collector 24. When voltage is supplied to the needle 23 from the voltage DC power supply 22 to create an electric field between the needle 23 and the collector while feeding a polymer solution to the needle 23 by using the syringe pump 21, a jet of the polymer solution charged at a conical surface end of the polymer solution suspended at the tip of the needle 23 is released. The released jet of the polymer solution flies in the air toward the collector 24 and simultaneously the organic solvent is evaporated from the polymer solution. Then, the charged continuous phase polymer fiber is accumulated on the collected 24 to prepare a nanofiber matrix 10.

In this electrospinning process, the control of concentration, viscosity and surface tension of the polymer solution, the spinning distance from the tip of the needle 23 to the collector 24, intensity of the electric field, spinning time, spinning environment, etc., can produce nanofibers having a desired thickness and shape.

After the nanofiber matrix 10 is prepared, it is subjected to ultrasonication and its detailed method will be described as follows.

Referring to FIG. 3, the prepared nanofiber matrix 10 is immersed in a solution 30 such as distilled water or the like, and sonic waves are applied to the solution 10 in which the nanofiber matrix 10 is immersed by using an ultrasonic transducer 32. Then, the molecules of the solution 30 are vibrated to infiltrate into spaces defined between the nanofibers 11 and exert a force to the nanofiber 11 so that nanofibers 11 entangled with each other are sparsely spaced. By doing so, the size of the pores between the nanofibers 11 is increased to cause the nanofiber matrix 10 to be expanded. This ultrasonication can increase the porosity and thickenss of the nanofiber matrix 10.

When the sonic waves are applied to the nanofiber matrix 10 immersed in the solution 30, the temperature of the solution 30 rises due to the frictions between the nanofiber and the molecules of the solution 30, between the nanofibers 11, and between the molecules of the solution 30. At this time, when the temperature of the solution 30 rises to a predetermined level or more, the nanofibers 11 may be induced to be deformed or damaged. In order to solve this problem, the sonic waves are preferably applied to the nanofiber matrix 10 in a state in which the solution 30 is cooled.

Preferably, the temperature of the solution 30 during the ultrasonication is in a range from 0° C. to 4° C. If the temperature of the solution 30 is less than 0° C., mobility of the molecules of the solution 30 during the application of sonic waves is deteriorated to cause expandability of the nanofiber matrix 10 to be reduced. On the contrary, if the temperature of the solution 30 exceeds 4° C., the suppressing effect of the temperature rise of the solution 30 is lowered.

A water tank 34 containing the solution 30 therein is received in a cooling container 30 containing ice 36 therein to cool the solution 30, and sonic waves are applied to the solution cooled by the ice 36, so that an excessive temperature rise of the solution can be suppressed and the nanofibers 11 can be prevented from being deformed or damaged. Besides such an ice cooling method, the water tank 34 containing the solution 30 therein is received in a cooling container whose temperature can be maintained at low temperature by a cooling device or the like, and ultrasonication is performed, so that the same cooling effect as in the ice cooling method can be obtained. In addition, when the water tank 34 itself is cooled by the cooling device, the temperature rise of the solution 30 can be suppressed during the ultrasonication.

After the ultrasonication treatment, when a natural polymer solution such as gelatin, chitosan or the like is applied on the nanofiber matrix and is freeze-dried, the properties of the natural polymer including excellent biocompatibility, biological activity, antimicrobial activity, and the like can be imparted to the three-dimensional nanofibrous scaffold.

A method other than the above-mentioned freeze-frying method may be used as a method for imparting the properties of the natural polymer to the three-dimensional nanofibrous scaffold. For example, when a mixture of the natural polymer and a synthetic polymer is added in the electrospinning process, the three-dimensional nanofibrous scaffold having all the properties of natural polymer and the property of the synthetic polymer can be obtained. Further, if the nanofiber matrix is prepared by electrospinning the synthetic polymer and then it is subjected to ultrasonication in a natural polymer solution such as an aqueous gelatin solution or an aqueous chitosan solution, the properties of the natural polymer can be imparted to the three-dimensional nanofibrous scaffold.

Hereinafter, the present invention will be described in further detail with reference to examples. It will be obvious to those skilled in the art that these examples are for illustrative purposes only and are not to be construed as limiting the scope of the present invention.

EXAMPLES

Fabrication of Three-Dimensional Nanofibrous scaffold for Tissue Regeneration

First, a PLLA polymer (Poly(L-lactic acid), RESOMER® L207 S,i.v.=1.5-2.0 dl/g, Boehringer Ingelheim Pharma GmbH & Co. Fine Chemical, Germany) was dissolved in HFIP(1,1,1,3,3,3-hexafluoro-2-propanol, TCI, TOKYO KASEI, Japan) as an organic solvent to thereby prepare a PLLA/HFIP polymer solution at a concentration of 0.10 g/mL (10 wt. %).

Next, the prepared polymer solution was loaded into a 5 ml glass syringe with a metal blunt-end needle (22G, Kovax-needle, Korea Vaccine Co., Ltd., Korea), and was electrospun on an aluminum foil covered rotating mandrel for 10 h while applying a voltage of 18 kV using a high-voltage DC power supply (Nano NC, Korea) with a 1 mL/hr feed rate and a 15 cm needle tip-to-collector. The needle tip was traversed horizontally along a distance of 10 cm at a speed of 2 cm/sec. By virtue of this electrospinning, a circular nanofiber matrix having a diameter of 15 mm and a thickness of 120 μm was prepared, and the resultant nanofiber matrix was placed under vacuum for 1 day at room temperature to remove residual solvent.

Thereafter, a circular nanofiber matrix was punched using a 15 mm metal punch (TCK, Korea) and prewetted by 70% ethanol for 1 min. The prewetted nanofiber was immersed in 10 ml of deionized distilled water (DDW) and ultrasonicated using an ultrasonicator (VCX 750, Sonics) at 4° C. to thereby fabricate a three-dimensional nanofibrous scaffold. In this case, the ultrasonication processing conditions for electrospun polymer nanofibers was adjusted as follows: sonication power: 150 W; sonication time: 1, 2, 5, 10 and 20 mins; and sonication energy: 20, 30 and 60 $J^{-1}$.

Analysis of Three-Dimensional Nanofibrous Scaffold for Tissue Regeneration

Figure 4:
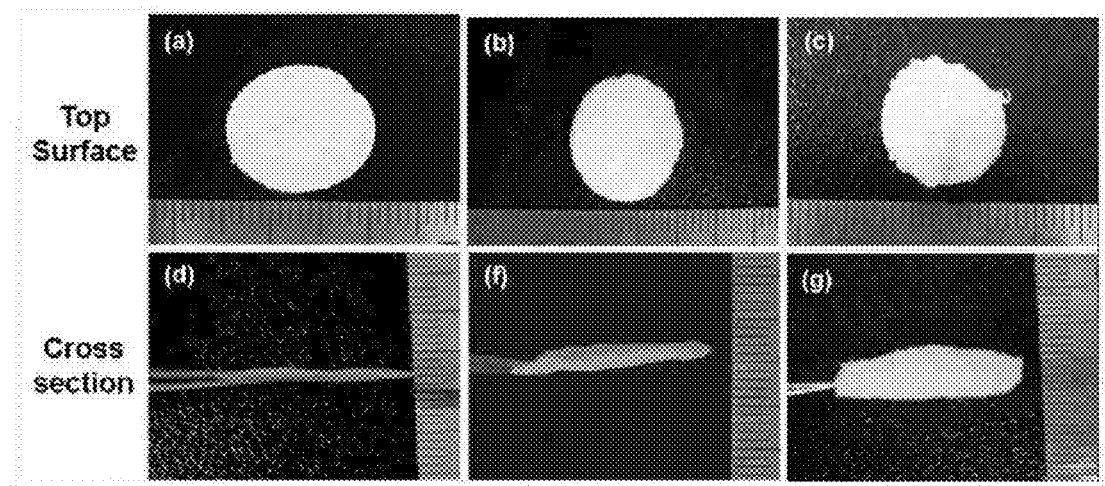
FIG. 4 is a photograph illustrating top surface and cross-sectional images of a nanofiber matrix and a three-dimensional nanofibrous scaffold according to an embodiment of the present invention.

FIG. 4 is a photograph illustrating top surface and cross-sectional images of a nanofiber matrix and a three-dimensional nanofibrous scaffold according to an embodiment of the present invention.

FIGS. 4(a) and 4(d) illustrate top surface and cross-sectional images of a nanofiber matrix prior to ultrasonication, FIGS. 4(b) and 4(e) illustrate top surface and cross-sectional images of an ultrasonicated three-dimensional nanofibrous scaffold after 1 min sonication, and FIGS. 4(c) and 4(f) illustrate top surface and cross-sectional images of an ultrasonicated three-dimensional nanofibrous scaffold after 10 mins sonication. It can be found from the photograph shown in FIG. 4 that there is a difference in thickness between ultrasonicated and non-ultrasonicated nanofiber matrices, and the thickness of the nanofiber matrix is increased as the sonication time is increased.

Figure 5:
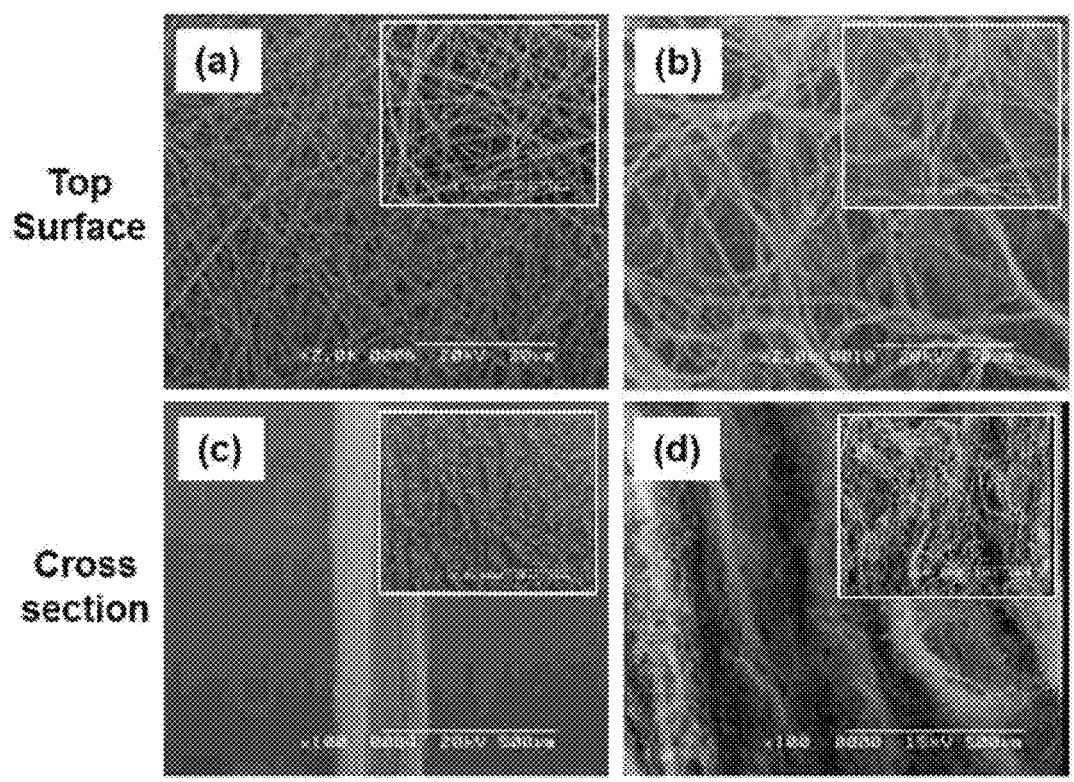
FIG. 5 is an SEM photograph illustrating top surface and cross-sectional images of a nanofiber matrix and a three-dimensional nanofibrous scaffold according to an embodiment of the present invention.
Figure 6:
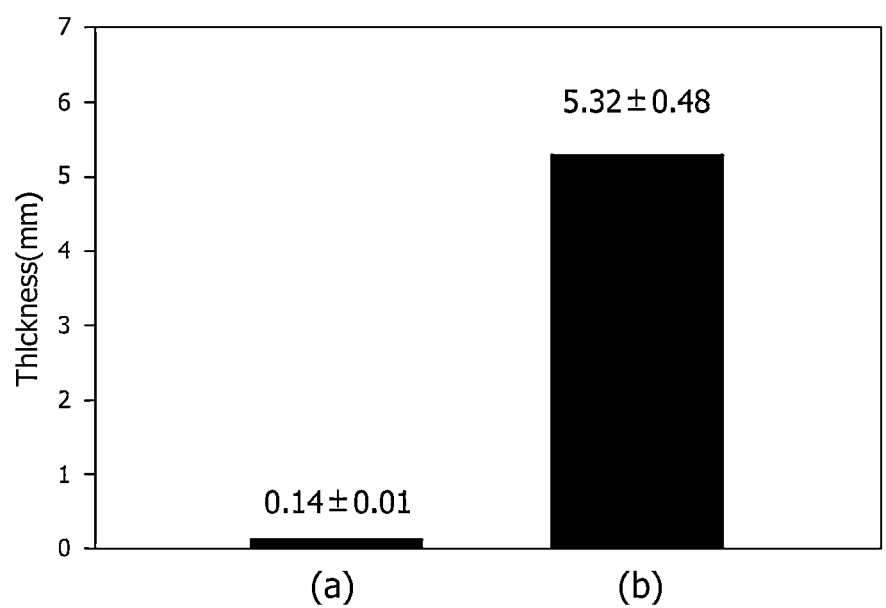
FIG. 6 is a graph illustrating the thicknesses of a nanofiber matrix and a three-dimensional nanofibrous scaffold according to an embodiment of the present invention.

FIG. 5 is an SEM photograph illustrating top surface and cross-sectional images of a nanofiber matrix and a three-dimensional nanofibrous scaffold according to an embodiment of the present invention, and FIG. 6 is a graph illustrating the thicknesses of a nanofiber matrix and a three-dimensional nanofibrous scaffold according to an embodiment of the present invention.

FIGS. 5(a) and 5(c) illustrate top surface and cross-sectional images of a nanofiber matrix prior to ultrasonication, FIGS. 5(b) and 5(c) illustrate top surface and cross-sectional images of an ultrasonicated three-dimensional nanofibrous scaffold. It can be found from FIG. 5 that the pore sizes between the nanofibers after ultrasonication are increased. In addition, it can be found from FIG. 6 that the thickness (a) of a non-ultrasonicated nanofiber matrix is 0.14 mm whereas the thickness (b) of an ultrasonicated nanofibrous scaffold is 5.32 mm, which indicates that the thickness of the nanofibrous scaffold can be increased by ultrasonication.

Figure 7:
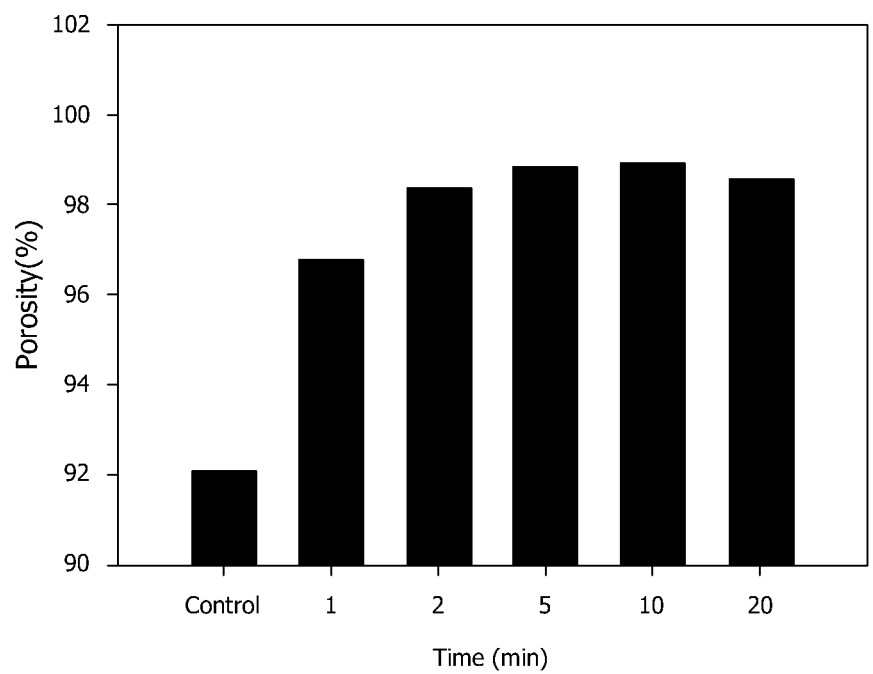
FIG. 7 is a graph illustrating a change in porosity of a three-dimensional nanofibrous scaffold according to the sonication time.
Figure 8:
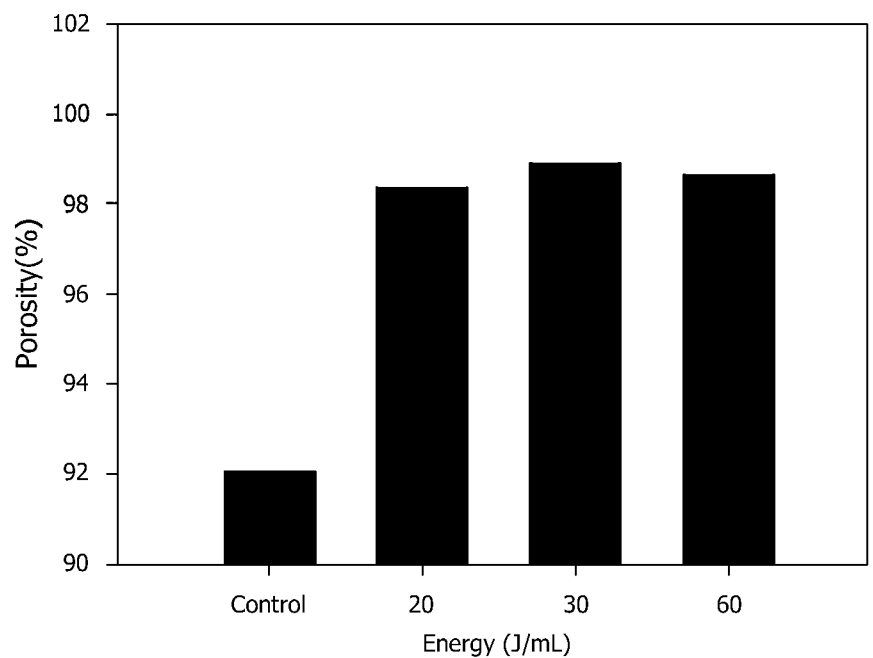
FIG. 8 is a graph illustrating a change in porosity of a three-dimensional nanofibrous scaffold according to the sonication energy.

FIG. 7 is a graph illustrating a change in porosity of a three-dimensional nanofibrous scaffold according to the sonication time, and FIG. 8 is a graph illustrating a change in porosity of a three-dimensional nanofibrous scaffold according to the sonication energy.

Here, porosity can be calculated using the following Equations 1 and 2:

$$\text{Density (g/cm}^3) = \frac{\text{mass (g)}}{\text{thickness (cm)} \times \text{area (cm}^2)} \quad \text{[Equation 1]}$$

$$\text{Porosity (\%)} = \left(1 - \frac{\text{density of scaffold (g/cm}^3)}{\text{density of PLLA (g/cm}^3)}\right) \times 100\% \quad \text{[Equation 2]}$$

First, the density of the three-dimensional nanofibrous scaffold can be calculated using Equation 1, and the porosity of the three-dimensional nanofibrous scaffold can be calculated using Equation 2.

It could be seen from a graph of FIG. 7 that although ultrasonication is performed only for 1 min, the porosity of the three-dimensional nanofibrous scaffold is increased up to 92% to 96%. In addition, it could be seen form the graph of FIG. 7 that when ultrasonication is performed for 5 mins, the porosity of three-dimensional nanofibrous scaffold is maximum whereas if sonication time exceeds 5 mins, the porosity thereof is not increased any more. Further, it could be seen from a graph of FIG. 8 that when the sonication energy of the three-dimensional nanofibrous scaffold is set to 30 $J \cdot mL^1$, the maximum porosity can be obtained.

As described above, according to the present invention, the nanofiber matrix prepared by using electrospinning is subjected to ultrasonication in a solution, so that a three-dimensional nanofibrous scaffold having increased porosity and thickness can be fabricated. A conventional scaffold entails a problem in that its pores are too small and its porosity is low, which makes it difficult to culture cells. On the contrary, the three-dimensional nanofibrous scaffold for tissue regeneration according to the present invention is advantageous in cell culture in that its pore size is large, its porosity is high, and thus its cellular infiltration is excellent.

Furthermore, the conventional prior art makes the control of the porosity ad thickness of the nanofiber matrix very difficult in the control of the electrospinning processing conditions whereas the present invention can implement a three-dimensional nanofibrous scaffold with improved thickness and porosity in a simple and low-cost manner.

It will be obvious to those skilled in the art that these examples are for illustrative purposes only and are not to be construed as limiting the scope of the present invention.

It should be understood that the spirit of the present invention is not limited to the embodiments described and illustrated herein. The scope of the present invention is defined only by the appended claims. It is apparent to those skilled in the art that various modifications and changes can be made thereto within the spirit of the invention. Therefore, the modifications and changes will fall within the scope of the present invention so long as they are apparent to those skilled in the art.

What is claimed is:

1. A method of fabricating a three-dimensional nanofibrous scaffold for tissue regeneration, the method comprising the steps of:
   producing a nanofiber matrix including a plurality of nanofibers entangled with each other from a polymer solution by electrospinning;

immersing the produced nanofiber matrix in a solution;

applying ultrasonication to the solution containing the produced nanofiber matrix, in a state in which the solution is cooled, to expand pores between the plurality of nanofibers and increase a thickness of the produced nanofiber matrix;

coating the expanded nanofiber matrix with a natural polymer; and freeze-drying the natural polymer-coated nanofiber matrix.

2. The method according to claim 1, wherein the natural polymer is selected from the group consisting of gelatin and chitosan.

3. The method according to claim 1, wherein in the step of applying ultrasonication to the solution, the solution is cooled with ice.

4. The method according to claim 1, wherein in the step of applying ultrasonication to the solution, sonic waves are applied to the solution in a state in which the temperature of the solution is 0° C. to 4° C.

5. The method according to claim 1, wherein the solution is a natural polymer solution.

6. The method according to claim 5, wherein the natural polymer solution is selected from the group consisting of an aqueous gelatin solution and an aqueous chitosan solution.

7. The method according to claim 1, wherein the polymer solution includes a synthetic polymer and a natural polymer.

8. A three-dimensional nanofibrous scaffold for tissue regeneration fabricated by a process comprising the steps of:

producing a nanofiber matrix including a plurality of nanofibers entangled with each other from a polymer solution by electrospinning;

immersing the produced nanofiber matrix in a solution;

applying ultrasonication to the solution containing the produced nanofiber matrix, in a state in which the solution is cooled, to expand pores between the plurality of nanofibers and increase a thickness of the produced nanofiber matrix;

coating the expanded nanofiber matrix with a natural polymer; and freeze-drying the natural polymer-coated nanofiber matrix.

* * * * *